United States Patent
Casset et al.

(10) Patent No.: US 6,714,820 B2
(45) Date of Patent: Mar. 30, 2004

(54) CYCLE TO CYCLE ADJUSTMENT OF THE STIMULATION AMPLITUDE FOR AN ACTIVE IMPLANTABLE MEDICAL DEVICE

(75) Inventors: Cyrille Casset, Paris (FR); Marcel Limousin, Paris (FR)

(73) Assignee: ELA Medical S.A., Montrouge (FR)

( * ) Notice: Subject to any disclaimer, the term of this patent is extended or adjusted under 35 U.S.C. 154(b) by 0 days.

(21) Appl. No.: 10/227,169

(22) Filed: Aug. 23, 2002

(65) Prior Publication Data

US 2003/0060855 A1 Mar. 27, 2003

(30) Foreign Application Priority Data

Aug. 28, 2001 (FR) .............................. 01 11147

(51) Int. Cl.[7] .............................................. A61N 1/362
(52) U.S. Cl. ........................................................ 607/28
(58) Field of Search ............................. 607/7–9, 11, 28

(56) References Cited

U.S. PATENT DOCUMENTS

| | | |
|---|---|---|
| 4,895,152 A | 1/1990 | Callaghan et al. |
| 5,350,410 A | 9/1994 | Kleks et al. |
| 5,411,533 A * | 5/1995 | Dubreuil et al. ............... 607/28 |
| 5,534,016 A * | 7/1996 | Boute ............................... 607/9 |
| 6,324,427 B1 * | 11/2001 | Florio ............................ 607/28 |

* cited by examiner

Primary Examiner—Mark Bockelman
(74) Attorney, Agent, or Firm—Orrick Herrington & Sutcliffe, LLP

(57) ABSTRACT

An active implantable medical device, in particular a pacemaker, defibrillator, cardioverter, or multisite device, having an improved cycle to cycle adjustment of the stimulation amplitude. The device stimulates the ventricle, adjusts the stimulation amplitude, periodically evaluates a capture threshold and defines a safety amplitude (Vs), and determines the detection or the loss of a capture on each cardiac cycle after stimulation with a given stimulation amplitude (V). Preferably, the device defines a capture amplitude (Vc) that is higher or equal to the capture threshold, but lower than the safety amplitude. The adjustment includes temporarily reducing the amplitude of stimulation below the safety amplitude toward the value of amplitude capture (Vc); checking, immediately after a stimulation at the reduced amplitude, the detection or the loss of capture (steps 12,14); in the event of a detection of capture, establishing for the next cardiac cycle the stimulation amplitude at the value of the capture amplitude (step 16); and, in the event of loss of capture, defining a new value, higher than the current capture amplitude (steps 44, 46).

9 Claims, 1 Drawing Sheet

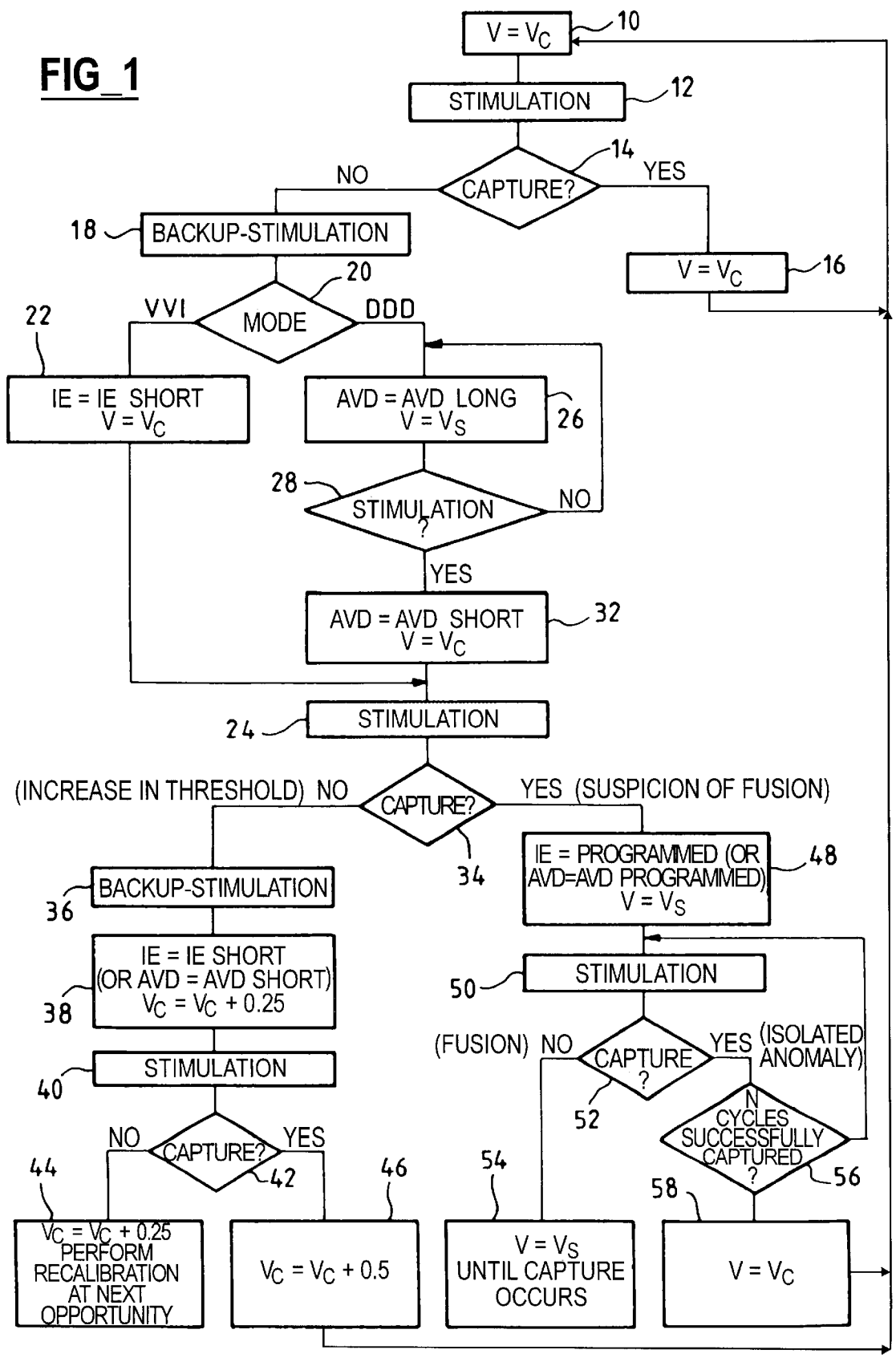

CYCLE TO CYCLE ADJUSTMENT OF THE STIMULATION AMPLITUDE FOR AN ACTIVE IMPLANTABLE MEDICAL DEVICE

FIELD OF THE INVENTION

The present invention is directed to "active implantable medical devices" as such devices are defined by the Jun. 20, 1990 directive 90/385/CEE of the Council of the European Communities, and more particularly to pacemaker, defibrillator, cardiovertor and/or multisite devices for the treatment of the disorders of the heartbeat. It more particularly relates to the adjustment of the amplitude voltage level of the stimulation pulses over the course of time.

BACKGROUND OF THE INVENTION

The stimulation pulse amplitude level of the cardiac cavities (ventricle or atrium) is a value typically ranging between 1.5 and 7.5 V, adjustable by step increments of 0.5 V. This amplitude must of course be sufficiently high to cause a depolarization of the myocardium, what is called "capture". It is, however, necessary to avoid values that are too high to spare the lifespan of the battery. In this regard, the stimulation energy applied, and thus the corresponding energy consumption of the device, is proportional to the square of the amplitude (and also to the duration) of the pulse.

The test for the threshold of stimulation effectiveness, or "threshold test," can be carried out at regular intervals, for example, every six hours. One such algorithm using an automatic test is described in particular in the WO-A-93/02741 and its corresponding U.S. Pat. No. 5,411,533 commonly assigned herewith to Ela Medical. The stimulation pulse amplitude is then adjusted on the basis of the threshold thus measured, with a large safety margin added: The adjusted level is generally twice the value of the measured threshold, and the adjusted level is limited by a minimum (typically 2.5 V) and by a maximum (typically 5.0 V). This particular adjusted level will be called thereafter "safety amplitude" and will be indicated by the labels Vs.

It is an object of the invention to minimize the stimulation pulse voltage, reducing it down to a level that is close to the threshold voltage (that is, the voltage below which there will be no more capture, also known as a loss of capture), by checking of course in a much more frequent way, typically with each cardiac cycle, whether the stimulation was effective so as to readjust the stimulation voltage as far as it can be reduced and/or to switch back to a voltage corresponding to the safety amplitude when appropriate. This reduced stimulation voltage that is close to the capture threshold will be called hereafter "capture amplitude" and will be indicated by the label Vc. This technique is particularly advantageous, because it makes it possible to avoid having to use the large safety margin for the stimulation pulse amplitude, and thus lengthens in a substantial way the lifespan of the battery. On the other hand, insofar as stimulation is made at a level that is close to that of the capture threshold, it is essential to operate a capture test "cycle to cycle", i.e., to examine at each cardiac cycle whether the stimulation pulse was effective rather than to test capture at periodic intervals, for example, every six hours as in the prior known devices. If a loss of capture is detected, a backup-stimulation pulse having a suitably large energy must be immediately applied (i.e., at the end of the 63 ms period following the stimulation that is determined to be ineffective) in order to compensate, without awaiting the absence of a depolarization of the myocardium. Moreover, the next stimulation pulse will be operated on the basis of the aforementioned safety amplitude, and the voltage level of the capture amplitude will be reevaluated to determine whether it is necessary to readjust it to be at a higher amplitude.

It is necessary, however, to take into account the fact that the detection of a loss of capture can actually be only the consequence of the occurrence of a "fusion", i.e., a stimulation intervening in a concomitant way with a spontaneous ventricular depolarization. Indeed, after an atrial stimulation, the detected ventricular event (the well known "QRS" complex) can be either the direct result of the stimulation, taking into account the latency time existing between the two events, or a spontaneous QRS complex occurring in the same temporal window (known as a "fusion"). The occurrence of a fusion can have a noxious effect from the hemodynamic point of view, because of the presence of two very close myocardial excitations, of which one is useless hemodynamically.

In the case of a capture test, even if a fusion does not have a hemodynamic effect, it is nevertheless likely artificially to produce an increase of the value of the measured capture threshold as compared to the real threshold of the patient, with for a consequence a readjustment of the stimulation amplitude to an excessive level that is maintained at least for several hours. Although this excessive level is not in itself dangerous, it does constitute an unnecessary consumption of battery energy and will reduce the lifespan of the implant.

It is therefore desirable, during the detection of a loss of capture, to discriminate between: a true loss of capture following a natural increase in the capture threshold, the occurrence of a proven fusion, or a simple a typical cycle (post-atrial ventricular detection, too rapid cycle or extrasystole). The last two cases do not justify an immediate revision of the stimulation amplitude level.

OBJECTS AND SUMMARY OF THE INVENTION

The present invention, therefore, is broadly directed to a method and apparatus for determining the capture amplitude according to the detected threshold, taking account of possible occurrence of fusion or a typical cycles, and ensuring if necessary an automatic switch to the safety amplitude.

More particularly, the present invention is directed to an improved device of a known type including: means for stimulating the ventricle by delivering to the heart one or more stimulation pulses, each pulse having a predetermined amplitude and a duration; means for adjusting the amplitude of the stimulation pulse to be delivered; means for evaluating at periodic intervals a capture threshold and for defining a corresponding safety amplitude from the capture threshold; and means for detecting capture cycle to cycle, to determine the detection or the loss of capture on each cardiac cycle after a stimulation at a given stimulation amplitude.

In a characteristic manner of the invention, it is further envisaged to include means for defining a capture amplitude at a level that is function of the capture threshold, and that is equal to or greater than the capture threshold but lower than the safety amplitude, wherein the means for adjusting the stimulation pulse amplitude includes means for reducing temporarily the stimulation amplitude below the safety amplitude and close to the aforementioned capture amplitude value; for checking, immediately after a stimulation using said reduced amplitude, the detection or the loss of capture; and, in the event of a detection of capture, establishing for the next cardiac cycle a stimulation amplitude at the value of the capture amplitude; and, in the event of loss of capture, defining a new stimulation amplitude value that is greater than the then current capture amplitude value.

In a preferred embodiment, the means for defining the capture amplitude establishes the capture amplitude at a level that is equal to the capture threshold increased by a fixed increment, for example, one step of adjustment of the stimulation amplitude.

In a further preferred embodiment, the means for adjusting is operated so that, in the event of a determined loss of capture and before the stimulation amplitude voltage is set at the safety amplitude, it performs a discrimination between, on the one hand, an occurrence of a fusion or an a typical cycle, and, on the other hand, a rise in the capture threshold. The discrimination may in particular be made by a reduction of the escape interval or the atrio-ventricular delay (depending on the pacing mode being used), followed by a detection of capture on a following stimulation operated with a stimulation amplitude corresponding to the capture amplitude.

In a more preferred embodiment, the means for adjusting the stimulation amplitude value is operated, in the event of the occurrence of a fusion or of an a typical cycle, to perform an additional discrimination between, on the one hand, the occurrence of a fusion, and, on the other hand, the occurrence of an a typical cycle. Such a discrimination may be made, in particular, by lengthening the escape interval or the atrio-ventricular delay, followed by detecting capture on a consecutive stimulation operating with a stimulation amplitude value corresponding to the safety amplitude. In the event of fusion, the stimulation amplitude is preferably established at the value of the safety amplitude and, in the event of a determined a typical cycle, the re-establishment of the capture is detected over a predetermined number of successive consecutive cycles and, in such a case, the stimulation amplitude is established at the value of the capture amplitude for the next cardiac cycle.

BRIEF DESCRIPTION OF THE DRAWING

Further advantages, features and characteristics of the present invention will become apparent to a person of ordinary skill in the art in view of the following discussion, made with reference to the annexed FIGURE, which is a flow chart of the various stages of an algorithm used by a device in accordance with a preferred embodiment of the present invention.

DETAILED DESCRIPTION OF THE INVENTION

Primarily, the present invention proposes, unlike the prior known techniques where the stimulation amplitude is readjusted at regular intervals, to operate a capture test "cycle to cycle," i.e., to examine with each cardiac cycle whether a stimulation pulse delivered was effective, and to readjust in consequence, if necessary, the stimulation amplitude.

More precisely, this technique is used by employing the following operations in succession:
  to control the ventricular capture threshold periodically,
  to choose a ventricular stimulation amplitude according to the result of this capture test,
  to check at each stimulated cycle if the capture is correct,
  to modify the stimulation amplitude if the capture is not confirmed, and
  to try to reveal spontaneous conduction if one is present.
These various steps are used in turn in three successive phases, the first two of which intervene in the same way as in the prior known case of a capture test at regular intervals:

a) a preliminary calibration, to evaluate and remove the effect of the polarization of the cardiac probe to the heart/electrode interface by determining a reference value, b) measurement of the capture threshold compared to the previously obtained reference value, and c) control of the capture on each cycle where a ventricle is stimulated, and a possible readjustment of the stimulation amplitude.

The steps (a) and (b) of calibration and measurement of the capture threshold are identical to those operated in the known devices, for example, in the manner described in the above mentioned WO-A-93/02741 and U.S. Pat. No. 5,411, 533, to which reference is made and as is well known to those skilled in the art. The present invention does not modify the fundamental manner in which each one of these two steps are used. In summary, for the calibration step (a) the pacemaker measures the evoked potential (or, more precisely, the average of several values of evoked potential) for different amplitude pulses, for example, two pulses at 2 V and 4 V. An algorithm then determines a regression line between these two values and the ordinate at origin, and intercept, of this line. The threshold of effectiveness of the capture is fixed at a value function of this intercept, for example, 75% of the value of the intercept (because the intercept over-estimates in fact the real polarization value), and the threshold thus calculated will constitute the reference value for the measurement of the minimum threshold value.

Step (b) of the threshold test determines the crossing of the capture threshold so as to adjust the stimulation pulse amplitude level compared to the capture threshold, i.e., to the minimal level allowing a capture.

This adjustment is obtained by a progressive controlled reduction of the amplitude level over several successive cycles, a detection of the disappearance of the capture, and then an establishment of the amplitude at a level slightly higher than the threshold corresponding to the disappearance or loss of capture. If the algorithm were held normally (absence of a typical cycles, of atrial extrasystoles, of too fast rate), it determines a value corresponding to the last found effective capture threshold, called the "capture threshold". In addition, the algorithm determines the safety amplitude value Vs, for example, equal to the double the threshold value, this value being limited by a minimum (typically 2.5 V) and by a maximum (typically 5.0 V).

Step (c), characteristic of the present invention, concerns, after having thus determined a safety amplitude Vs, the calculation of a second amplitude that is lower, than one will call the "capture amplitude" labeled Vc. This capture amplitude will be, in this example, defined as being equal to the level of the measured capture threshold increased by 0.5 V, with a minimal value of 1.0 V, that is to say:

Vc (in volts)=Max (1.0; capture threshold+0.5).

where "max" means "the larger of". The algorithm then will control the pacemaker so as to apply stimulation pulse with this reduced amplitude Vc:
  if a following capture is detected, then Vc will constitute the stimulation amplitude,
  if, on the contrary, this reduced level causes a loss of capture, the safety amplitude Vs will be used, and the behavior of the myocardium will be analyzed to determine whether it is necessary to increase the initially evaluated capture amplitude level Vc.

The detail of a process for performing the algorithm is illustrated on FIG. 1. First of all (step 10), the stimulation amplitude V is fixed at the amplitude level of a definite capture amplitude Vc as indicated above, namely Vc=Max (1; capture threshold+0.5). Of course, if the value of the capture amplitude Vc were corrected following a preceding iteration of the algorithm, then it is the corrected value that will be used here. The device then applies a stimulation pulse with the capture amplitude thus defined (step 12) and tests the presence or the absence of a capture (step 14). The detection of a capture is carried out, in a way in itself known, by measurement of the wave R in a 63 ms window following the delivery of the pulse. If a capture is detected, the algorithm keeps Vc as the stimulation amplitude (step 16). If, on the contrary, a loss of capture is detected, first of all a backup-stimulation with a larger energy is immediately applied, i.e., at the end of the 63 ms window following the ineffective stimulation, in order to compensate for the insufficient stimulation without awaiting the absence of depolarization of the myocardium (step 18).

The following stage concerns modifying certain stimulation parameters so as to let be expressed, if it is present, the spontaneous ventricular rate of the patient. It will be then possible to distinguish between, on the one hand, a true loss of capture due to an increase in the effective capture threshold, and, on the other hand, a loss of capture due to another cause, for example, the occurrence of a fusion or an a typical cycle. This modification can be operated in two manners, according to the operating mode of the pacemaker (tested at step 20).

In the case of a pacemaker functioning in a VVI or an equivalent mode (VVI, VVT, DDI), the modification relates to the duration of the ventricular escape interval (IE), which is in this case reduced, for example, by a 63 ms value, such that the stimulation amplitude is always maintained with the value of capture amplitude Vc (step 22). The myocardium is then stimulated (step 24) and the device then diagnoses the capture or the loss of capture (step 34).

For a pacemaker operating in a double-chamber DDD mode or equivalent (DDD, DDTV, DD-CAM, VDD, etc.), thus acting at the same time on the atrium and on the ventricle, the parameter modified is the atrio-ventricular delay (AVD), which is forced to a long value, to leave time for the spontaneous ventricular rate, if it is present, to express itself naturally, with an amplitude V=Vs ensuring the capture (step 26).

If, with these new parameters, a stimulation occurs (step 28), the stimulation amplitude is restored to the value of capture amplitude Vc and the AVD is forced to a reduced value, typically 63 ms (step 32). The myocardium is then stimulated as previously (step 24), and the device then diagnoses the capture or the loss of capture (step 34). If, at step 28, no stimulation intervenes, then the algorithm returns at step 26. If no capture is diagnosed at step 34, this means that there was increase in the threshold, and that the capture amplitude Vc must be readjusted. In this case, first of all a backup-stimulation is applied (step 36). Then, while keeping the modified values of parameters EI or AVD (EI short or AVD short, as at steps 22 or 32), the capture amplitude Vc is increased by a step, typically a step of 0.25 V (step 38). A new stimulation is delivered on the basis of these last parameters (step 40) and a test of capture is carried out (step 42).

If the loss of capture remains, the capture amplitude Vc is once again increased and a phase of calibration can be started again so as to initialize the totality of the parameters of the algorithm of adjustment of the amplitude of stimulation. However, it is made so that the calibration is not started again more than three times in six hours, and not less than one hour before the preceding calibration (step 44).

If a capture was diagnosed at step 42 after the increase in the capture amplitude Vc at step 38, then the algorithm establishes as capture amplitude Vc, for the future, a new value determined at step 38, i.e., the last determined minimal amplitude Vc which made it possible to obtain a capture, with a safety margin of 0.5 V (step 46).

If, at step 34, a capture was diagnosed after modification of the escape interval at step 22 or of the atrio-ventricular delay AVD at step 32, this means that the threshold probably did not increase, but that the loss of capture at the step 14 was due to a phenomenon such as a fusion or an a typical cycle. To discriminate these two possibilities, the algorithm restores the escape interval or the atrio-ventricular delay with the programmed value for that parameter and chooses as the stimulation amplitude the safety amplitude Vs, such as it was defined at the time of the calibration phase (step 48). A stimulation is then applied on these bases (step 50) and the presence or the absence of a consecutive capture is diagnosed (step 52).

In the event of loss of capture, this means that one is truly in situation of fusion, and the stimulation amplitude level is maintained at the value of the safety amplitude Vs until a capture can be diagnosed (step 54). The safety amplitude is selected during some number N of cycles, to avoid disturbing the algorithm if one would be in the case of a situation of intermittent fusion. If, on the contrary, a capture was diagnosed at step 52, the algorithm continues by checking that one has a number N (typically, N=3) of successive cycles of capture without fusion (step 56) and, if such is indeed the case, the stimulation level is then restored to the former value of the capture amplitude Vc (step 58).

In a general way, the above description presupposes that the test of capture of steps 14, 34, 42 and 52 always provides a unambiguous result. There are, however, situations in which it is not possible to check the capture or to obtain an unquestionable diagnosis of the presence or loss of the capture, for example, in the cases of ventricular post-atrial detection, or in the presence of too fast cycles, or of ventricular extrasystoles. In this case, the following stimulation will be operated with the capture amplitude Vc as stimulation level, because it is this value Vc which was loaded in the corresponding control register for setting the voltage level. To increase the stimulation energy to the appropriate level, the pulse width will be increased, for example, to 0.98 ms instead of 0.49 ms. With the following cycle, the device will change in any event, by precaution, to the safety amplitude Vs for next stimulation. After that, the stimulation level will be reduced to Vc, and so on until the algorithm can diagnose in an un-ambiguous manner the capture or the loss of capture.

It will be appreciated that the present invention is preferably implemented in the form of software instructions for performing the functions described by the foregoing steps of the algorithm discussed, and implemented in a microprocessor controlled active implantable medical device having circuits for generating stimulation pulses and delivering each pulse with a defined width and amplitude, and for monitoring cardiac activity (spontaneous and stimulated) and identifying intervals between such activity. Suitable microprocessor controlled device include, for example, the commercial Talent™, Defender™ and Alto™ devices available from the assignee hereof, Ela Medical, Montrouge France. Advantageously, the present invention can be downloaded to an already implanted device by an external programmer, in a conventional manner, as software instructions to modify the operation of the already implanted device, for such devices that are able to receive software instructions and to modify its operation in response thereto. Suitable software instructions to produce the desired control signals for the conventional circuit structures for monitoring cardiac activity, controlling pacing, and setting and delivering stimulation pulses as discussed herein in a microprocessor controlled device are deemed to be well within the ability of a person of ordinary skill in the art.

One skilled in the art will appreciate that the present invention can be practiced by other than the described embodiments, which are presented for purposes of illustration and not of limitation.

We claim:

1. An active implantable medical device comprising:

means for stimulating the ventricle, to deliver to the heart a stimulation pulse presenting a predetermined pulse amplitude and duration, means for adjusting the stimulation pulse amplitude, means for periodically evaluating a capture threshold and defining a corresponding safety amplitude, said safety amplitude being greater than said capture threshold;

means for detecting a capture cycle to cycle, and determining a detection or a loss of capture on each cardiac cycle after a stimulation pulse having a given stimulation amplitude; and means for defining a capture amplitude that is in a range between the capture threshold and the safety amplitude;

wherein the means for adjusting the stimulation pulse amplitude further comprises:

means for temporarily reducing the stimulation amplitude below the safety amplitude toward the aforementioned capture amplitude; and means for checking, immediately after a stimulation with said reduced stimulation amplitude, the detection or loss of capture, and, in the event of a detected detection of capture, establishing for a next cardiac cycle the stimulation amplitude at the capture amplitude, and in the event of a detected loss of capture, increasing the capture amplitude.

2. The device of claim 1, wherein the means for defining said capture amplitude further comprises means for increasing the capture amplitude by a fixed increment.

3. The device of claim 2, wherein the fixed increment comprises an increment of a step having a constant value.

4. The device of claim 1, wherein the adjusting means further comprises means for discriminating between, on the one hand, an occurrence of a fusion or an a typical cycle, and, on the other hand, a rise in capture threshold, said discriminating means being responsive to a detected loss of capture and operable before said adjustments means establishes the stimulation amplitude at the safety amplitude.

5. The device of claim 4, where the means for discriminating further comprises means for reducing one of an escape interval and an atrio-ventricular delay, and means for detecting a capture on a consecutive stimulation having a stimulation amplitude corresponding to the capture amplitude.

6. The device of claim 4, wherein the adjusting means further comprises, second means for discriminating, responsive to a detected fusion or a typical cycle, between an occurrence of a fusion and an occurrence of an a typical cycle.

7. The device of claim 6, where the second means for discriminating comprises means for lengthening said reduced one escape interval and an atrio-ventricular delay, and means for detecting capture on a consecutive stimulation having a stimulation amplitude corresponding to the safety amplitude.

8. The device of claim 6, wherein the adjusting means further comprises means for establishing the stimulation amplitude at the value of the safety amplitude in response to a discriminated fusion.

9. The device of claim 6, wherein the adjusting means further comprises means for detecting a re-establishment of capture over a predetermined number of later successive cycles and, in response thereto, for establishing the stimulation amplitude at the value of the capture amplitude for the next cardiac cycle.

* * * * *